United States Patent [19]

Bodor

[11] Patent Number: 4,622,218

[45] Date of Patent: * Nov. 11, 1986

[54] TESTICULAR-SPECIFIC DRUG DELIVERY

[75] Inventor: Nicholas S. Bodor, Gainesville, Fla.

[73] Assignee: University of Florida, Gainesville, Fla.

[*] Notice: The portion of the term of this patent subsequent to Oct. 30, 2001 has been disclaimed.

[21] Appl. No.: 475,493

[22] Filed: Mar. 15, 1983

Related U.S. Application Data

[63] Continuation-in-part of Ser. No. 379,316, May 18, 1982, Pat. No. 4,479,932.

[30] Foreign Application Priority Data

Jun. 14, 1982 [JP] Japan .................. 57-101940

[51] Int. Cl.$^4$ .................. A61K 49/00; A61K 31/455; A61K 33/44; A61K 31/47; C07J 1/00; C01G 41/06; C07C 87/28; C07D 239/02

[52] U.S. Cl. ........................ 424/9; 424/258; 424/263; 424/264; 424/266; 424/267; 260/239.5; 260/397.4; 564/381; 564/382; 514/19; 514/176; 514/11; 514/311; 514/356; 514/277; 514/357; 514/492

[58] Field of Search ............... 424/177, 94; 546/316; 564/381, 382; 260/297.4, 239.5, 112.5; 514/176

[56] References Cited

U.S. PATENT DOCUMENTS 4,479,932 10/1984 Bodor ...................................... 424/9

OTHER PUBLICATIONS

Bodor, N. et al. (including Richard Roller and Sally Selk) J. Pharm. Sci., V. 67, No. 5, May 78, pp. 685-687.
Bodor, N. et al. (including Hassan H. Farag) Science, V. 214, No. 4527, Dec. 1981, pp. 1370-1372.
Bodor, N. et al. (including Hassan H. Farag) J. Medicinal Chem., V. 26, Mar. 83, pp. 313-317.
Cowie et al. J. Phys., V. 171, p. 1976 (London) 1964.
Kurmano, M. *Actal Physiol. Scand.*, V. 71, p. 125, 1967.

*Primary Examiner*—Thomas G. Wiseman
*Assistant Examiner*—Robin Lyn Teskin
*Attorney, Agent, or Firm*—Kerkam, Stowell, Kondracki & Clarke

[57] ABSTRACT

Testicularly acting drug species are site-specifically/-sustainedly delivered to the testes by administering to a male in need of such treatment a pharmacologically effective amount of the target drug species [D] tethered to a reduced, blood-testis barrier penetrating lipoidal form [D—DHC] of a dihydropyridine⇌pyridinium salt type redox carrier, e.g. 1,4-dihydrotrigonelline. Oxidation of the dihydropyridine carrier moiety in vivo to the ionic pyridinium salt type drug/carrier entity [D—QC]$^+$ prevents elimination thereof from the testes, while elimination from the general circulation is accelerated, resulting in significant and prolongedly sustained testicular-specific drug activity, whether ascribable to the cleavage of the [D—QC]$^+$ entity and sustained release of the drug [D] in the testes and/or to [D—QC]$^+$ itself.

37 Claims, 1 Drawing Figure

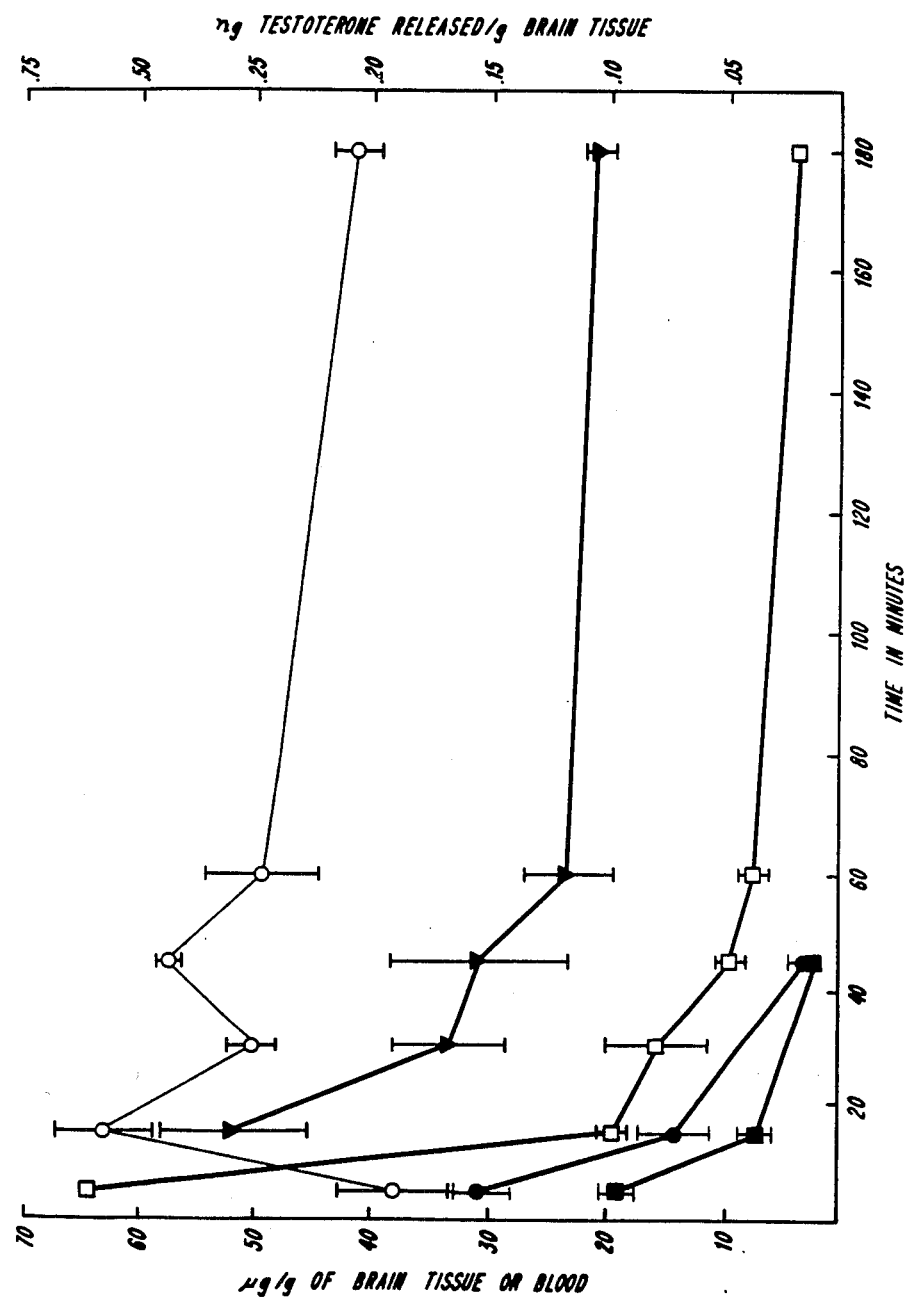

TESTICULAR-SPECIFIC DRUG DELIVERY

CROSS-REFERENCE TO RELATED APPLICATION

This application is a continuation-in-part of my earlier copending application, Ser. No. 379,316, filed May 18, 1982, now U.S. Pat. No. 4,479,932 hereby expressly incorporated by reference in its entirety and relied upon.

BACKGROUND OF THE INVENTION

1. Field of the Invention

The present invention related to a dihydropyridine ⇌ pyridinium salt type of redox system for the site-specific or sustained delivery (or both) of a wide variety of drug species to the testes. More especially, this invention relates to the discovery that a biologically active compound coupled to a lipoidal carrier moiety comprising a dihydropyridine nucleus readily and easily penetrates the blood-testis barrier ("BTB") and attains increased levels of concentration in the testes; oxidation of the dihydropyridine carrier moiety in vivo to the ionic pyridinium salts prevents its elimination from the testes, while elimination from the general circulation is accelerated, and subsequent cleavage of the quaternary carrier/drug species at least in part results in sustained delivery of the drug in the testes, or otherwise provides significant and prolongedly sustained testicular-specific pharmacological activity, with attendant facile elimination of the carrier moiety.

2. Description of the Background Art

In my aforenoted copending application, the Ser. No. 379,316, now U.S. Pat. No. 4,479,932 detailed reference is made to the well established fact that the delivery of drug species to the brain is ofttimes seriously limited by transport and metabolism factors and, more specifically, by the functional barrier of the endothelial brain capillary wall deemed the blood-brain barrier, BBB. Site-specific delivery and sustained delivery of drugs to the brain are even more difficult, and to date no useful simple or generic techniques to achieve such phenomena are known to the art.

Accordingly, acutely serious need exists in this art for a truly effective generic but nonetheless flexible method for the site-specific, or sustained delivery, or both, of drug species to the brain, and a major object of the invention disclosed and claimed in my said '316 copending application is the provision of just such a generic method for the site-specific/sustained delivery of centrally acting drug species to the brain, by administering to a patient in need of such treatment an effective amount of the target drug species [D] tethered to a reduced, blood-brain barrier penetrating lipoidal form [D—DHC] of a dihydropyridine ⇌ pyridinium salt type redox carrier. Oxidation of the dihydropyridine carrier moiety in vivo to the ionic pyridinium salt type drug/carrier entity [D—QC]+ prevents elimination thereof from the brain, while elimination from the general circulation is accelerated, and subsequent cleavage of the quaternary carrier/drug species results in sustained delivery of the drug [D] in the brain and facile elimination of the carrier moiety [QC]+.

Another object of said '316 invention is to provide for brain-specific drug delivery utilizing a dihydropyridine ⇌ pyridinium salt carrier type redox system, which drug/carrier system is characterized by enhanced drug efficacy and decreased toxicity. Indeed, consistent therewith systemic toxicity is significantly reduced by accelerating the elimination of the drug/quaternary carrier system, and even central toxicity is reduced by providing a low level, sustained release of the active drug species in the brain.

In capsule summary, my '316 invention features a dihydropyridine ⇌ pyridinium salt carrier redox system for the specific and sustained delivery of drug species to the brain according to the following Scheme 1:

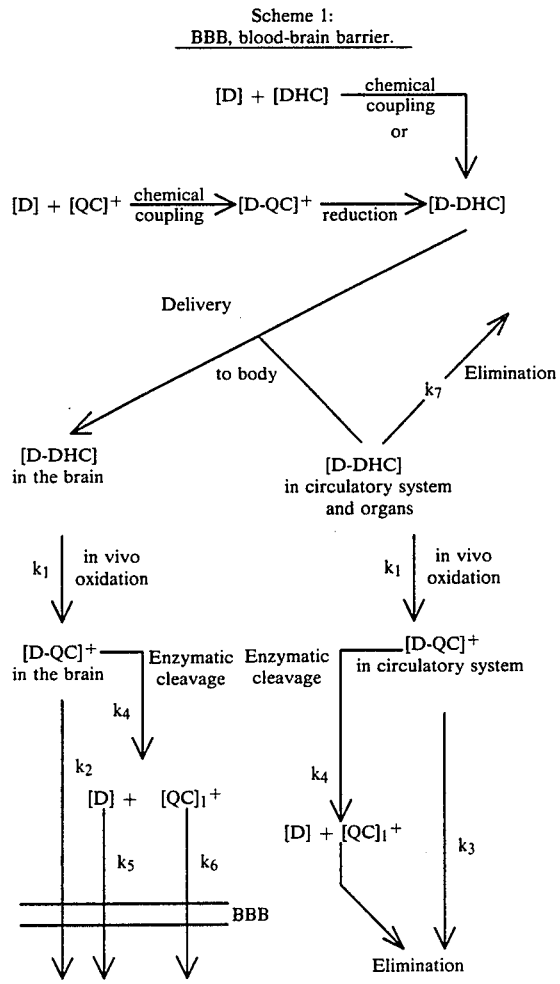

Scheme 1:
BBB, blood-brain barrier.

Consistent with the foregoing Scheme 1, any drug species [D] is coupled to a quaternary pyridinium salt carrier [QC]+ and the prodrug [D—QC]+ which results is then reduced chemically to the lipoidal dihydro pro-prodrug form [D—DHC]. Alternatively, the drug species [D] can be directly coupled to the dihydro carrier [DHC] in certain instances to yield said pro-prodrug form [D—DHC]. After administration of the [D—DHC] in vivo, it is rapidly distributed throughout the body, including the brain. The dihydro form [D—DHC] is then in situ oxidized (rate constant, $k_1$) (by the NAD ⇌ NADH coenzyme system) to the ideally inactive original [D—QC]+ quaternary salt prodrug, which, because of its ionic, hydrophilic character, is rapidly eliminated from the general circulation of the body, while the blood-brain barrier prevents its elimination from the brain ($k_3 >> k_2$; $k_3 >> k_7$). Enzymatic cleavage of the [D—QC]+ that is "locked" in the brain effects a sustained delivery of the drug species [D], followed by its normal elimination ($k_5$), metabolism. A properly selected carrier [QC]+ will also be rapidly eliminated from the brain ($k_6 \gg k_2$). Because of the facile elimination of [D—QC]+ from the general circulation, only minor amounts of drug are released in the body ($k_3 \gg k_4$); [D] is released primarily in the brain ($k_4 > k_2$). The overall result is a brain-specific, sustained release of the target drug species. Cf. Bodor et al, *Science*, 214, 1370 (1981); *C&EN*, 24 (Dec. 21, 1981).

The existence of a blood-testis barrier (BTB) by which some substances are prevented from being carried into the seminiferous tubules long has been suspected [P. P. H. Bruyn, R. C. Robertson and R. S. Farr, *Anat. Rec.*, 108, 279 (1950); R. J. Goldacre and B. Sylven, *Nature* (London) 184, 63 (1959); R. J. Goldacre and B. Sylven, *J. Cancer*, 16, 306 (1962); T. S. Ro and H. Busch, *Biochem. Biophys Acta* (Amst) 108, 317 (1965)]. Some investigators have suggested a similarity between the BBB and the BTB [A. T. Cowie, A. K. Lascelles and J. C. Wallace, *J. Physiol.* (London), 171, 176 (1964); R. E. Mancini, O. Vilar, B. Alvarez and A. C. Seiguer, *J. Histochem. Cytochem.*, 13, 376 (1965); M. Kormano, *Acta Physiol. Scand.*, 71, 125 (1967); M. Kormano, *Histochemic,* g, 327 (1967)]. Don W. Fawcett, Lee V. Leak and Paul M. Heidger, Jr., *J. Reprod. Fert. Suppl.* 10, 105 (1970) have suggested that the permeability barrier is not in the testis capillary walls because these more closely resemble the capillaries of muscle than those involved in the BBB. M. Dym and Don W. Fawcett, *Biology of Reproduction,* 3, 308 (1970) concluded that the epithelioid contractile layer around the seminiferous tubules constitutes a significant permeability barrier augmented by an apparently more efficient barrier involving tight cell-to-cell junctions between sertoli cells that inhibits penetration of substances through the germinal epithelium. Despite such histological differences, pharmacokinetic studies [K. Okumura, I. P. Lee and R. L. Dixon, *J. Pharmacol. Exp. Therap.*, 194, 89 (1975); I. P. Lee and R. L. Dixon, *Environmental Health Perspectives,* 24, 117 (1978)] have demonstrated that the functional BTB resembles the BBB in transport characteristics, both depending on lipid solubility and molecular size. Thus, delivery of drug species to the testes is often seriously limited by the blood-testis barrier. Site-specific delivery and sustained delivery of drugs to the testes are even more difficult. To date, no useful simple or generic techniques to achieve such results are known to the art. It is thus apparent that a serious need exists in this art for a method for the site-specific and/or sustained delivery of drug species to the testes to elicit the desired therapeutic, e.g. hormonal or tumor-inhibiting, response.

SUMMARY OF THE INVENTION

It has now been found, and which constitutes a major object of this invention, that my novel chemical delivery system based upon a dihydropyridine⇌pyridinium salt type redox carrier per my copending application, U.S. Ser. No. 379,316, now allowed U.S. Pat. No. 4,479,932 is uniquely well suited for the design of an effective testicular-specific chemical delivery system, for the site-specific and/or sustained eliciting of significant drug response in the testes. In one aspect, the present invention thus provides, as an effective drug delivery system, compounds having the formula

[D—DHC]     (I)

and non-toxic pharmaceutically acceptable salts thereof, wherein [D] is a testicularly acting drug species and [DHC] is the reduced, biooxidizable, blood-testis barrier penetrating, lipoidal form of a dihydropyridine⇌pyridinium salt redox carrier. In another aspect, the present invention provides compounds having the formula

[D—QC]+     (II)

wherein [D] is a testicularly acting drug species and [QC]+ is the hydrophilic, ionic pyridinium salt form of a dihydropyridine⇌pyridinium salt redox carrier.

Also according to this invention, there is hereby provided a generic method for specific and/or target enhanced delivery to the testes of a wide variety of testicularly acting drug species, such testicular-specific drug delivery being effected via the bidirectional transport of the drug species into and out of the testes by means of dihydropyridine⇌pyridinium salt carrier type redox systems.

DETAILED DESCRIPTION OF THE INVENTION

By "testicularly acting drug species" as used herein, there is intended any drug which is capable of exerting a useful pharmacological effect when delivered to the testes. Generally speaking, those centrally acting drug species contemplated by my parent copending '316 application for delivery to the brain can likewise be delivered to and concentrated in the testes utilizing the instant dihydropyridine⇌pyridinium salt carrier type redox system; any such centrally acting drugs which exert a therapeutic or other useful biological effect when delivered to the testes are considered to be within the ambit of the present invention.

Exemplary of the drugs contemplated for delivery in accord with the present invention are antibiotics/antibacterials, antiviral agents, anticancer agents, hormonal agents and analgesics. The antibiotics/antibacterials can be, for example, sulfonamides, e.g. sulfanilamide, sulfadiazine, sulfalene and sulfacetamide; penicillins, e.g. ampicillin, amoxicillin and carbenicillin; cephalosporins, e.g. cephalexin; tetracyclines, such as tetracycline and methacycline; and other antibacterials, such as nalidixic acid and phenazopyridine hydrochloride. Among the antiviral agents, there can be mentioned ribavirin and aciclovir (ACV). The drugs used in cancer chemotherapy contemplated for use herein include nitrogen mustards, such as chlorambucil and melphalan; folic acid antagonists, such as methotrexate and aminopterin sodium; platinum coordination complexes, e.g. cisplatin analogues; antibiotic cancer agents, such as dactinomycin, mitomycin C and doxorubicin; podophyllotoxin and its derivatives; purine and pyrimidine antagonists, e.g. thioguanine; alkaloids, such as vincristine sulfate and vinblastine sulfate; urea derivatives, such as hydroxyurea; and hormonal anticancer agents such as cortisone and sex hormones. Among the hormonal agents contemplated for use herein are pituitary gonadotropins, such as follicle stimulating hormone (FSH), which maintains spermatogenesis and may be used to treat male infertility and cryptorchism; non-pituitary gonadotropins, such as human chorionic gonadotropin (HCG), which may be used for treatment of cryptorchism or hypogonadism in the male; adrenal cortical hormones, particularly glucocorticoids, which may be used in the treatment of inflammation (and possibly also in neoplasm), such as, for example, hydrocortisone, betamethasone, dexamethasone, flumethasone, fluprednisolone, meprednisone, methyl prednisolone, prednisolone, prednisone and triamcinolone; agents for male fertility inhibition, e.g. agents which impair gametogenesis or otherwise hamper sperm production, such as N,N'-bis(dichloracetyl)-1,8-octamethylene diamine; androgens, e.g. testosterone and methyltestosterone, agents of this type being useful for treating male hypogonadism, cryptorchism and the male climateric, as well as for maintaining or improving normal sexual function in the male and preventing decline in testicular function; and antiandrogens, e.g. cyproterone, which may be of use in male contraception and depression of male sexual behavior, especially in veterinary practice. Analgesics contemplated for use herein include narcotic analgesics such as morphine, hydromorphone, levorphanol and oxymorphone, agents of this kind being of use in the treatment of testicular pain, such as that associated with testicular cancer. Other testicularly acting drug species will be apparent to those skilled in the art. Presently preferred drug species contemplated for administration utilizing the present dihydropyridine⇌pyridinium salt carrier type redox system are the hormonal agents, principally the androgens, i.e. testosterone and its close analogues such as methyltestosterone; and the anticancer agents, especially those known to be useful in the treatment of testicular cancer, i.e. chlorambucil, melphalan, methotrexate and cisplatin-type compounds.

It too will be appreciated that by "dihydropyridine carrier" or "[DHC]", there is intended any nontoxic carrier moiety comprising, containing or including the dihydropyridine nucleus, whether or not a part of any larger basic nucleus, and whether substituted or unsubstituted, the only criterion therefor being capacity for both BTB-penetration and in vivo oxidation thereof to the corresponding quaternary pyridinium salt carrier [QC]+. As aforesaid, the ionic pyridinium salt drug/carrier prodrug entity [D—QC]+ which results from such in vivo oxidation is prevented from efflux from the testes, while elimination from the general circulation is accelerated. Subsequently, the covalent or equivalent bond coupling the drug species [D] to the quaternary carrier [QC]+ is metabolically cleaved which results in sustained delivery of the drug [D] in the testes and facile elimination of the carrier moiety [QC]+. Such "covalent or equivalent bond" between the drug and the quaternary carrier can be a simple direct chemical bond, e.g., an amide, an ester, or any other like bond, or same can even be comprised of a linking group or function, e.g., a thiazolidine bridge or a peptide linkage, typically necessitated when the drug species is not susceptible to direct chemical coupling to either the dihydropyridine carrier or the quaternary carrier. Nonetheless, the bond in the formulae [D—QC]+ and [D—DHC] is intended to be, as is hereby defined as inclusive of all such alternatives. And the cleavage of the [D—QC]+ prodrug to sustainedly deliver the drug species [D] in the testes with concomitant facile elimination of the carrier moiety [QC]+ is characteristically enzymatic cleavage, e.g., by esterase, amidase, cholinesterase, hydrolytic enzyme, or peptidase, albeit any type of in testis cleavage which might result, whether enzymatic, metabolic or otherwise, of course remains within the ambit of this invention. Thus, the drug release rate controlling parameter of the subject pro-prodrugs is imparted simply via the cleavable bonding between drug and carrier, and not by any release rate controlling substituent(s).

It also will be appreciated that the term "lipoidal" as used herein is intended to designate a carrier moiety which is lipid-soluble or lipophilic.

The expression "non-toxic pharmaceutically acceptable salts" as used herein generally includes the non-toxic salts of compounds of the invention formed with nontoxic, pharmaceutically acceptable inorganic or organic acids HX. For example, the salts include those derived from inorganic acids such as hydrochloric, hydrobromic, sulfuric, sulfamic, phosphoric, nitric and the like; and the salts prepared from organic acids such as acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, methanesulfonic, toluenesulfonic and the like.

In one embodiment according to this invention, simple nontoxic carrier systems [D—QC]+⇌[D—DHC] are envisaged, utilizing a wide variety of models for D, such as those above outlined. Representative such carrier systems and models are:

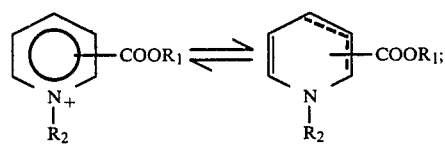

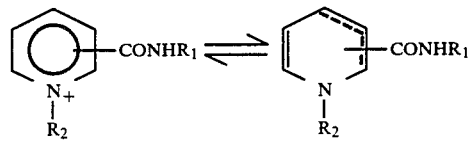

wherein $R_2$ is simply alkyl, e.g. $CH_3$, or benzyl, albeit virtually any other effective substituent is intended. Exemplary of such simple carrier systems are N-alkyl nicotinamide and nicotinate ester derivatives, tethered to such drug species as melphalan and testosterone. The trigonelline (N-methylnicotinic acid) system is quite effective as a carrier; it also is readily eliminated from the circulation and is virtually non-toxic.

Indeed, the present invention provides a flexible arsenal of dihydropyridine⇌pyridinium salt redox carriers for the site-specific/sustained delivery of virtually any testicularly acting drug species to the testes. Moreover, any dihydropyridine/pyridinium salt redox carrier entity is contemplated and intended hereby generically, and any such carrier moiety need not be, and is not derivatized with a drug release rate controlling substituent critically tailored to meet, or be coordinated with, the chemical nature and delivery requirements of the particular drug species sought to be preferentially administered to the testes. As utilized herein, the term "carrier" is to be understood as connoting just such a non-derivatized, non-drug/carrier coordinated entity, for consistent herewith it is the "carrier" entity itself and not the nature of any activity or release rate controlling/modifying substituent which is responsible for providing the desired testicular-specific result.

Additional examples of such redox carriers include the quaternary pyridinium alcohols (1), the analog isoquinoline acid and alcohol systems (2), and multi-charged delivery forms, exemplified by structure 3 (D represents drug, Z a covalent link) and obviously the corresponding dihydro forms.

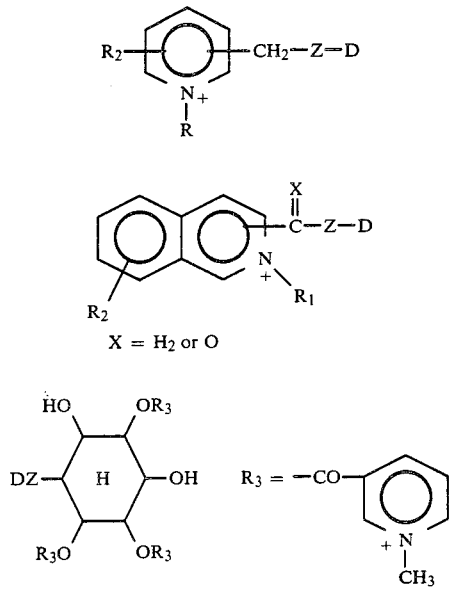

Yet other redox carriers include those comprising an acidic chain directly linked to the heterocyclic nitrogen, in quaternary or tertiary amine form. Also the hydroxide type carriers, e.g., the glucosamine analog indicated below. Representative are:

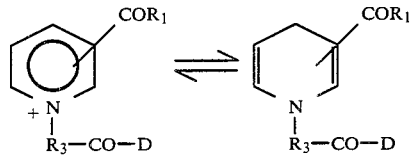

$R_1$ = $NH_2$; $OR_2$; and the like
$R_2$ = alcohol residue
$R_3$ = $(CH_2)_n$ n = 1-10 or $C_1$-$C_{12}$ branched alkyl, aryl-alkyl, and the like
D = drug—$NH_2$ or —OH;

Preparation:

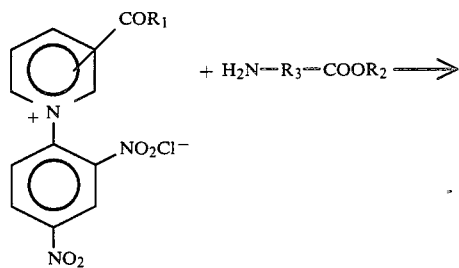

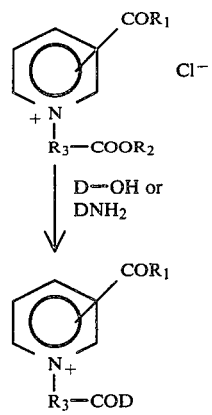

Method of: H. Lattre et al., Annalen, 579, 123 (1953).

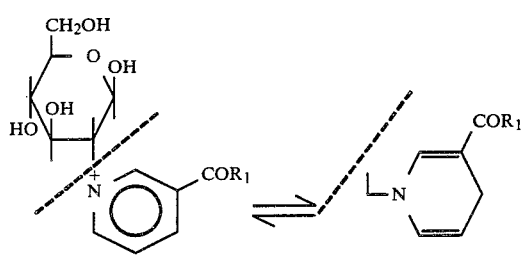

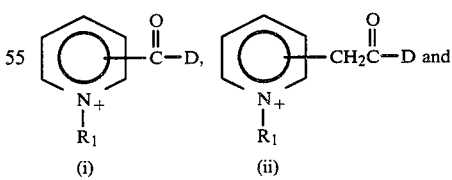

Generally preferred dihydropyridine⇌pyridinium salt redox carriers for use in the present invention include the following (where D represents the drug), and obviously the corresponding dihydro forms:

(a) the pyridinium systems

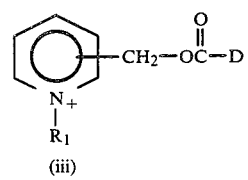

in which the depicted substituent is in the 2-, 3- or 4-position, and $R_1$ is $C_1$–$C_7$ alkyl or $C_7$–$C_{10}$ aralkyl, preferably methyl or benzyl;

(b) the pyridinium system

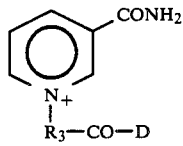
(iv)

in which $R_3$ is $C_1$ to $C_3$ alkylene, i.e. $(CH_2)_n$ where $n=1-3$;

(c) the isoquinolinium and quinolinium systems

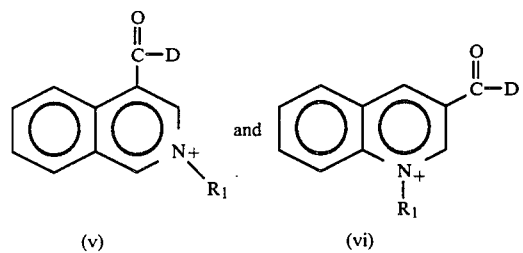
(v)     (vi)

in which $R_1$ is defined as above; and (d) the quinolinium and isoquinolinium systems

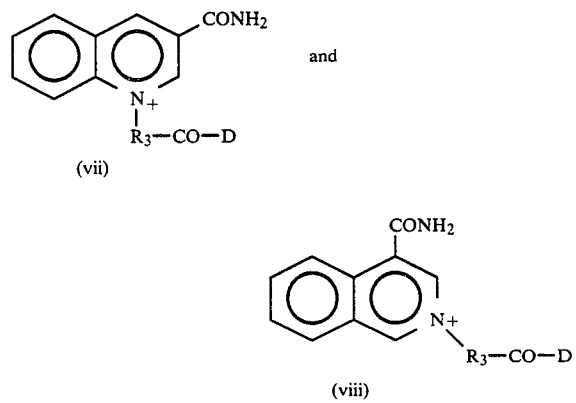
(vii)

(viii)

in which $R_3$ is defined as above. The corresponding dihydro forms of the foregoing preferred pyridinium salts are depicted below, wherein the position and identity of the structural variables are as indicated above.

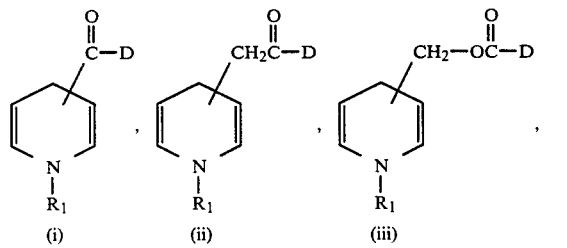
(i)    (ii)    (iii)

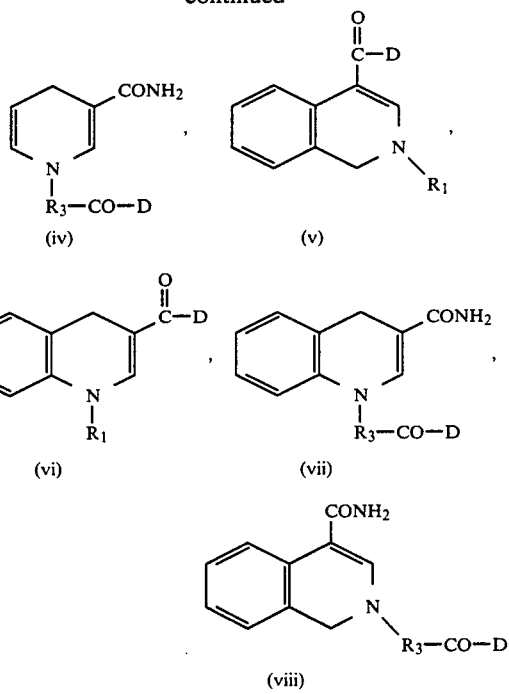
(iv)     (v)

(vi)     (vii)

(viii)

Naturally, selection of the particular dihydropyridine⇌pyridinium salt redox carrier to be used will depend on the chemical structure of the specific drug involved. And not only should the nature of the functional group which is to be linked to the carrier system be considered in selecting the carrier, but the manner in which the ultimate compound is prepared should be tailored to the presence of any other reactive groups in the molecule. The following examples of specific drug/carrier combinations and their manner of synthesis are set forth for the purpose of illustration only and are not to be considered limitative in any way whatsoever.

Thus, in one specific illustration, the selected drug is testosterone and the selected carrier system is trigonelline⇌dihydrotrigonelline; according to this embodiment, testosterone is reacted with nicotinoyl chloride, the resultant ester is then quaternized with methyl iodide, and the quaternary iodide is then reduced with $Na_2S_2O_4$ to afford the testosterone-CDS (chemical delivery system)

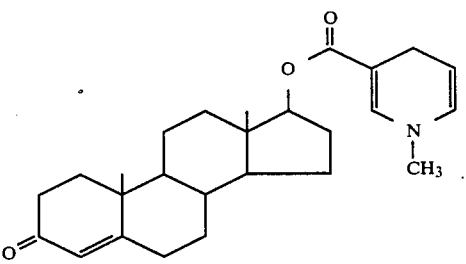

Another specific illustration involves selecting melphalan and the same type of carrier system as above, but forming an amide rather than an ester linkage. Thus, melphalan is converted to its hydrobromide, which is reacted with nicotinic acid to afford the amide having the formula

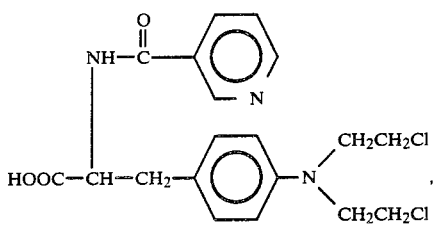

which can be esterified, if desired (to increase lipoidal characteristics), followed by, when the ethyl ester is prepared, quaternizing same with methyl iodide to form

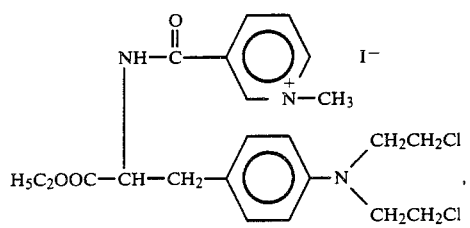

which can then be reduced to afford the melphalan-CDS

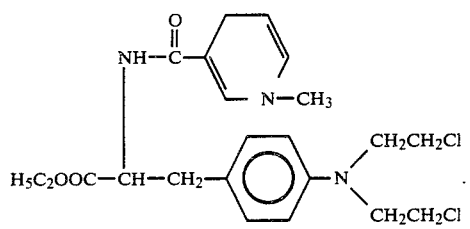

As one of several alternative schemes, melphalan can be derivatized by first esterifying it, e.g. to convert the carboxy function to the ethyl ester, then reacting the resultant malphanaln ethyl ester with nicotinoyl chloride to form the amide of the formula

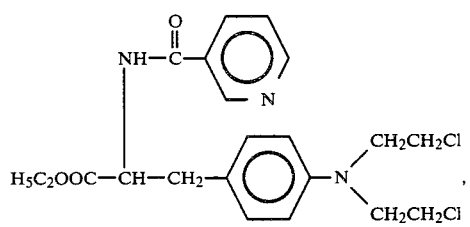

which can then be quaternized and the quaternary salt subsequently reduced as indicated above to afford to same melphalan-CDS as depicted above.

Yet another specific illustration utilizes chlorambucil as the target drug, in which case the desired nicotinic acid carrier system is linked to the drug via a bridging group. Thus, nicotinic acid can be reacted with an appropriate di- or polyhydroxy compound such as ethylene glycol, propylene glycol or inositol and the resultant intermediate is linked via its free hydroxy group(s) to the carboxylic acid function of chlorambucil. That intermediate is then quaternized and the quaternary salt is reduced to afford the chlorambucil-CDS. In the case of nicotinic acid and ethylene glycol starting materials, the chlorambucil-CDS has the formula

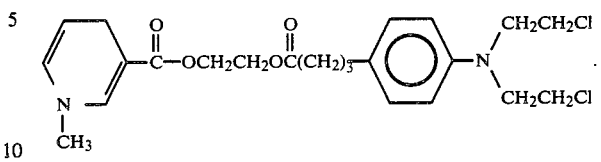

On the other hand, when a polyhydroxy compound is reacted with nicotinic acid in the first step, a variety of products are possible. Thus, for example, when inositol is used, the final product may contain anywhere from 1 carrier/5 drug residues to 5 carrier/1 drug residue. In the case of the inositol trinicotinate intermediate

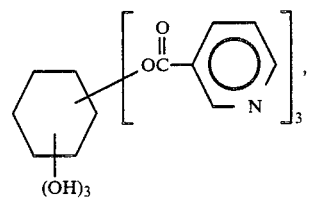

conditions for reacting same with chlorambucil can be selected so that one, two or three of the hydroxy functions react with the acid. When all three hydroxys react, the ultimate chlorambucil-CDS has the formula

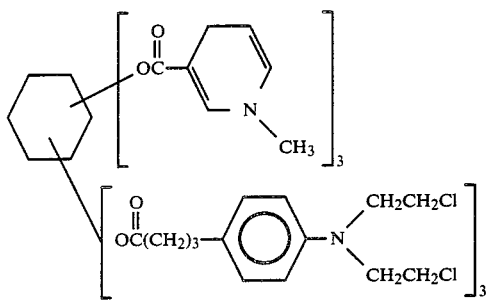

and contains 3 drug residues and 3 carrier groupings.

As another example, methotrexate, which has the structural formula

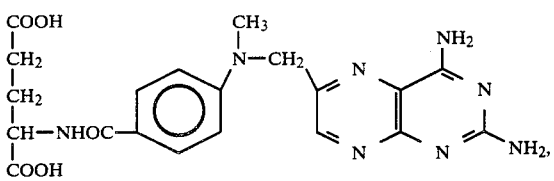

can be derivatized similarly to chlorambucil via its carboxy function(s), e.g. utilizing the inositol trigonellinates.

As a further example, podophyllotoxin and its derivatives can be linked to a carrier system of this invention. These drugs can be represented by the structural formula

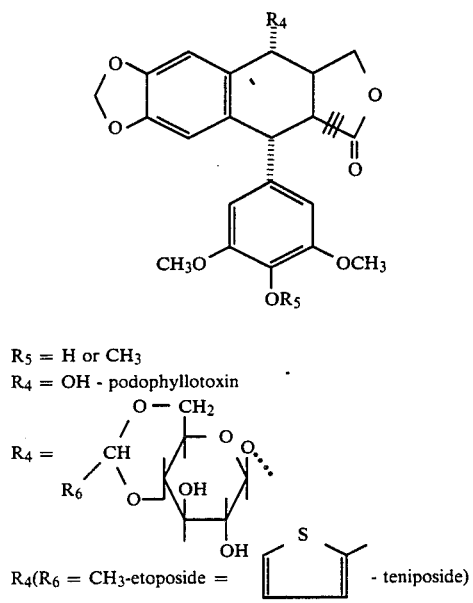

$R_5 = H$ or $CH_3$
$R_4 = OH$ - podophyllotoxin $R_4 = $ (glycoside structure)

$R_4(R_6 = CH_3$-etoposide = (thiophene) - teniposide)

and can be derivatized by reacting the hydroxy group in podophyllotoxin ($R_4=OH$) or the hydroxy groups in the glycosidic portions in $R_4$ with acidic type redox carriers, e.g. in a manner analogous to the testosterone-CDS depicted above. Known cisplatin analogues, in which typically the amino groups have been replaced with organic radicals, can be similarly derivatized according to the invention, the method of choice depending on the nature of the functional groups in the organic radicals.

The rationale of the present invention can be graphically illustrated with reference to the drug testosterone. The 17β-(1,4-dihydrotrigonelline) ester of testosterone, having formula Ia depicted in Scheme 2 below, by virtue of its good lipid solubility, crosses not only the BBB but also the BTB in the male. As shown in Scheme 2, biological oxidation to the corresponding quaternary derivative causes a "lock in" of the corresponding ionic, hydrophilic product in the testes of male animals, as well as in the brain. Conversely, oxidation in locales not involving a permeability barrier would favor rapid clearance from the blood because the quaternary derivative (IIa) is excreted more rapidly than the unoxidized form (Ia). Thus, oxidation favors accumulation of (IIa) in the brain and testes while yielding minimal blood levels. A subsequent, slow hydrolysis to free testosterone in the testes (as in the brain) therefore would provide a site-specific, prolonged testosterone action and minimal peripheral effects. Although $K_8$ should be much greater than $K_9$ and $K_5$ should be much greater than $K_4$, the slow rates of quaternary hydrolysis should assure a sustained release of testosterone in both testes and brain while yielding minimal levels in blood and other tissues. It is also expected that trigonelline released in the brain and testes by the hydrolytic process would be excreted easily and at comparable rates.

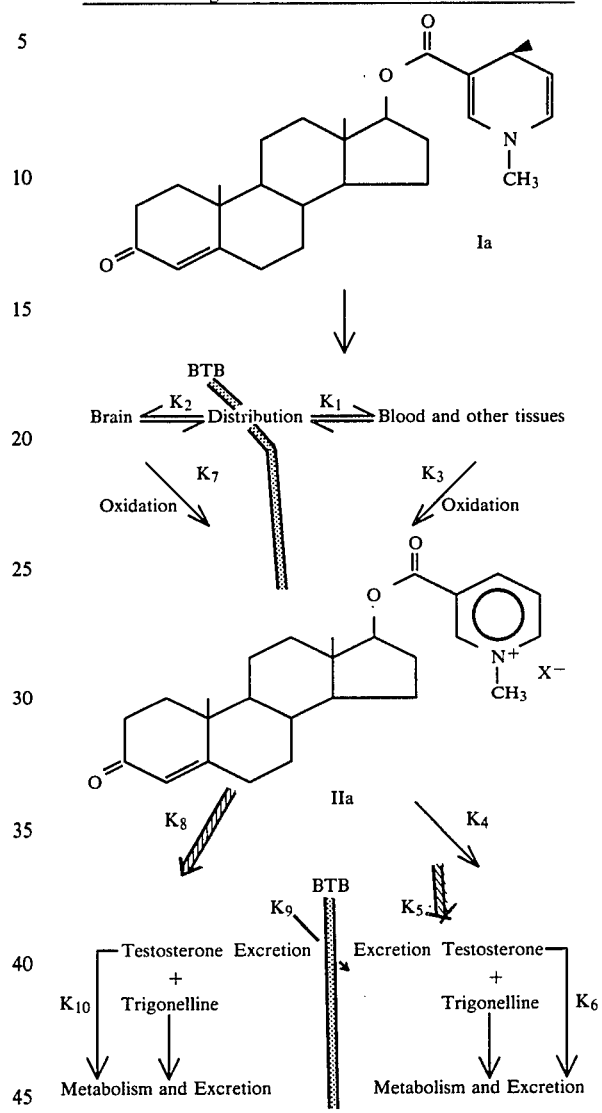

Scheme 2
Testosterone trigonellinate and the BTB, blood-testis barrier.

Suitable nontoxic pharmaceutically acceptable carriers for use with the topic compounds [D—DHC], e.g., those less toxic than the target drug species themselves, will be apparent to those skilled in this art. Compare, for example, Remington's Pharmaceutical Sciences, 4th Edition (1970). Obviously, the choice of suitable carriers will depend upon the exact nature of the particular dosage form selected, as well as upon the identity of the active drug species [D]. The therapeutic dosage ranges for administration of the compounds according to this invention will generally be the same as, or less than those characteristically used in this art for administration of the known drug species [D], per se. Naturally, such therapeutic dosage ranges will vary with the size of the patient, the condition for which the [D—DHC] compound is administered, the particular dosage form employed, and the like. The quantity of given dosage form needed to deliver the desired dose of [D] will of course depend upon the concentration of [D—DHC] in any given pharmaceutical composition/dosage form thereof.

The ability of the topic compounds to cross the BTB in the male and to be "locked into" the testes allows administration of the drug in a site-specific manner. A combination of the present dihydropyridine⇌pyridinium salt redox system with a sustained release system will further enhance this site-specificity. Thus, a preferred embodiment of the invention comprises formulating the [D—DHC] compound or its salt utilizing a sustained release carrier system and/or route of administration capable of slowly releasing the chemical, e.g. sustained release tablets and capsules for oral administration; subcutaneous injection, or implantation of drugs in solid pellet form (for example, distributed in a biodegradable polymer); intramuscular injection of the compound in solution in oil or suspended in a repository vehicle; a transdermal delivery device or form such as an ointment to be applied locally to the desired site (when the drug is susceptible of delivery through the skin) and the like. The rate of release of compound from the sustained release system should be comparable to the rate of in vivo oxidation of the dihydro form of the redox system in order to achieve the greatest degree of enhancement of specificity.

In order to further illustrate the present invention and the advantages thereof, the following specific examples are given, it being understood that same are intended only as illustrative and in nowise limitative.

In the examples immediately to follow, all melting points were taken on a Mel-Temp apparatus and are not corrected. Elemental analyses were performed at Atlantic Microlab, Inc., Atlanta, Ga. Infrared spectra were determined by using a Beckman Acculab 1 double-beam recording spectrophotometer. NMR spectra were determined by means of Varian T60A or FX100 spectrometers. All chemical shifts reported are in $\delta$ units (parts per million) relative to tetramethylsilane. Ultraviolet absorbance spectra were determined using a Cary Model 210 spectrophotometer. HPLC analyses were performed on a Beckman 345 ternary liquid chromatograph with Model 112 solvent delivery system, Model 210 injector, Model 160 absorbance detector and Model 421 controller.

EXAMPLE 1

Preparation of Testosterone nicotinate (compound 1):

Thionyl chloride (2 ml) was added to 0.7 g (5.7 mmol) of nicotinic acid and the mixture was refluxed for 3 hrs. Excess thionyl chloride was removed under reduced pressure. To the cold residue, 10 ml of dry pyridine was added, followed with 1.44 g (5.0 mmol) of testosterone. The mixture was heated with continuous stirring at 100° C. over a water bath for 4 hrs. Pyridine was removed in vacuo and 5 ml of methanol was added to the oily residue. The mixture was cooled and the solid that crystallized was filtered and recrystallized from methanol/acetone mixture to give 1.4 g of 1 as white crystals (yield 71%), m.p. 187°–188°. This intermediate was used directly for the synthesis of the chemical delivery system.

EXAMPLE 2

Preparation of
17β-[(1-Methyl-3-pyridiniumcarbonyl)oxy]androst-4-en-3-one iodide (compound 2)
(Testosterone-17-nicotinate N-methyl iodide)

To a solution of 1.0 g (2.5 mmol) of testosterone nicotinate 1 in 15 ml of acetone, 1 ml of methyl iodide was added and the mixture was refluxed overnight. The yellow solid that separated was removed by filtration, washed with acetone and crystallized from methanol/ether to yield 1.25 g (92% yield) of pure 2 as yellow crystals, m.p. 215°–220° C. (dec.). U.V. (CH$_3$OH) $\epsilon$270 nm (shoulder) $\epsilon$=4579; 240 (shoulder) $\epsilon$=19375. NMR (CDCl$_3$) $\delta$10.0–8.3 (ms, 4H, pyridinium protons), 5.73 (s, 1H, C$_4$ testosterone proton), 4.86 (s, 3H, +N—CH$_3$), 2.40–1.06 (ms, 26H, testosterone skelton protons). Analysis calculated for C$_{26}$H$_{34}$INO$_3$: C, 58.32; H, 6.40; N. 2.62. Found: C, 58.17; H, 6.48; N, 2.60.

EXAMPLE 3

Preparation of
17β-[(1,4-Dihydro-1-methyl-3-pyridinylcarbonyl)oxy]androst-4-en-3-one (compound 3)

To an ice cold solution of 1.1 g (2 mmol) of testosterone nicotinate N-methyl iodide 2 in 150 ml of deaerated 10% aqueous methanol, 0.67 g (8 mmol) of sodium bicarbonate and 1.37 g (8 mmol) of sodium dithionite were added. The mixture was stirred for 20 minutes and the pale yellow solid which separated was filtered, washed with water and dried over P$_2$O$_5$ under vacuum. Wt. 0.82 g (98% yield), m.p. 172°–175° C. UV (CH$_3$OH) $\lambda$356 nm, $\epsilon$=9511; ir (KBr) 1700, 1660 cm$^{-1}$ (two C=O stretching). NMR (d$_6$-DMSO) $\delta$6.90 (bs, 1H, C$_2$ dihydropyridine proton) 5.83–5.70 (m, 1H, C$_6$ dihydropyridine proton), 5.56 (s, 1H, C$_4$ testosterone proton), 4.7–4.33 (m, 1H, C$_5$ dihydropyridine proton), 3.26 (bs, 2H, C$_4$ dihydropyridine protons), 2.93 (s, 3H, N—CH$_3$), 2.5–83 (m, 26H, testosterone skelton protons with the angular methyl protons at 1.16 and 0.83). Analysis calculated for C$_{26}$H$_{35}$NO$_3$; C, 76.25; H, 8.61; N, 3.42. Found: C, 76.07; H, 8.65; N,3.38.

EXAMPLE 4

Analytical Methods

A high pressure liquid chromatograph (HPLC) method was developed for the studies of the degradation of the quaternary 2 and dihydropyridine derivative 3. The chromatographic analyses were performed on the Beckman described hereinabove. The absorbance detector was operated at 254 nm. A 15 cm×4.6 mm (internal diameter), 5 μm particle site ultrasphere reverse phase C$_{18}$ column (Altex), operated at ambient temperature, was used for all separations. The mobile phase used for the separation of the dihydropyridine derivative, its degradation products and oxidation products consisted of 0.002 M solution of 1-heptanesulfonic acid sodium salt (PIC B-7 Eastman Kodak) in CH$_3$CN, 0.01 M aqueous dibasic ammonium phosphate (7:3). At a flow rate of 2.0 ml/min, compound 2 had a retention time of 12 min and compound 3, 5 min. For the analysis of testosterone in the in vivo brain delivery studies, a solvent system consisted of 0.002 M solution of PIC B-7 in CH$_3$CN, 0.1 M aqueous dibasic ammonium phosphate (1:1). At a flow rate of 2.0 ml/min, testosterone had a retention of 3.3 min and compound 2 had a retention time of 36.5 min (very broad peak).

EXAMPLE 5

Chemical Oxidation Studies (i) By Silver Nitrate: 1 ml of 5% methanolic solution of the dihydropyridine compound 3 was added to 5 ml of saturated methanolic AgNO$_3$ solution. The mixture was shaken, left 10 minutes for complete oxidation, centrifuged and the UV spectrum checked.

(ii) By Hydrogen Peroxide: To a standardized solution of $H_2O_2$ (0.18 M) contained in a UV cuvette equilibrated at 37° C., a solution of dihydropyridine compound 3 was added to the sample cuvette to make a concentration of approximately $5 \times 10^{-6}$ M. The mixture was thoroughly mixed and monitored for the disappearance of the dihydropyridine maximum at 356 nm using a Cary 210 interfaced with an Apple II microprocessor and using an enzyme kinetic software package.

(iii) By Diphenylpicrylhydrazyl Free Radical: To 2 ml of $9.3 \times 10^{-5}$ M solution of 2,2-diphenyl-1-picrylhydrazyl free radical in acetonitrile, equilibrated at 26° C., 20 ml of $1.5 \times 10^{-2}$ M solution of the dihydropydine compound 3 in acetonitrile was added to make a final concentration of $1.48 \times 10^{-4}$ M. The mixture was monitored at 515 nm against a reference cuvette containing the same mixture in exactly the same concentrations, but previously prepared and left for at least 10 minutes and used as reference for $A_\infty$. The instrument used was a Cary 210 interfaced with an Apple II microprocessor and using an enzyme kinetic software package.

EXAMPLE 6

Determination of In Vitro Rates of Oxidation of Compound 3 in Biological Media

In Human Plasma:

The freshly collected plasma used was obtained at the Civitan Regional Blood Center, Inc. (Gainesville, Fla.) and contained about 80% plasma diluted with anticoagulant citrate phosphate dextrose solution U.S.P. The plasma was stored in a refrigerator and used the next day. 100 μl of a freshly prepared 0.024 M solution of compound 3 in DMSO were added to 10 ml plasma, previously equilibrated to 37° C. in a water bath and mixed thoroughly to result in an initial concentration of $2.4 \times 10^{-4}$ moles/liter. One ml samples of plasma were withdrawn every 20 minutes from the test medium, added immediately to 5 ml of ice cold acetonitrile, shaken vigorously and placed in a freezer. When all samples had been collected, they were centrifuged and the supernatants were filtered through nitrocellulose membrane filters (por 0.45) and analyzed by HPLC following appearance of 2 (Method A).

In Human Blood:

The freshly collected heparinized blood was obtained at the Civitan Regional Blood Center, Inc. (Gainesville, Fla.). The blood was stored in a refrigerator and used the next day. 100 μl of a freshly prepared 0.048 M solution of compound 3 in DMSO were added to 20 ml blood, previously equilibrated to 37° C. in a water bath and mixed thoroughly, to result in an initial concentration of $2.4 \times 10^{-4}$ moles/liter. One ml samples of blood were withdrawn from the test medium every 10 minutes, added immediately to 5 ml of ice cold acetonitrile, shaken vigorously and placed in a freezer. When all samples had been collected, they were centrifuged and the supernatants were filtered using nitrocellulose membrane filters (por 0.45) and analyzed by HPLC, following appearance of 2 and disappearance of 3.

In Rat Brain Homogenate:

The brain homogenate was prepared by the following method. Five female Sprague-Dawley rats were killed by decapitation and the brains were removed, pooled, weighed (total weight 9.2 g) and homogenized in 36.8 ml of aqueous 0.11 M phosphate buffer, pH 7.4. 100 μl of 0.024 M solution of compound 3 in DMSO were mixed with 20 ml of the homogenate, previously equilibrated to 37° C. in a water bath, to result in an initial concentration of $2.4 \times 10^{-4}$ moles/liter. Samples of 1.0 ml were withdrawn every 10 minutes from the test medium, added immediately to 5 ml of ice cold acetonitrile, shaken vigorously and placed in a freezer. When all samples had been collected, they were centrifuged and the supernatants were filtered through nitrocellulose membrane filter (por 0.45) and analyzed by HPLC (Method A).

EXAMPLE 7

In Vitro Determination of the Site-Specific Conversion or the Prodrug 2 to Testosterone:

A fresh brain homogenate was prepared as above described. 100 μl of 0.017 M solution of the quaternary compound 2 in methanol were mixed with 10 ml of the brain homogenate, previously equilibrated to 37° C. to result in an initial concentration of $1.7 \times 10^{-4}$ M. Samples of 1.0 ml were withdrawn every 20 minutes from the test medium, added immediately to 5 ml of ice cold acetonitrile and placed in a freezer. When all the samples had been collected they were centrifuged and the supernatant was filtered through nitrocellulose membrane filter (por 0.45) and analyzed for the quaternary compound 2.

EXAMPLE 8

In Vivo Brain Delivery of Testosterone Following Administration of the Dihydro Compound 3:

Female Sprague-Dawley rats of average weight of 225±10 g were used. The rats were anaesthetized with IM injection of Innovar ® (0.13 ml/kg) and the external jugular was exposed. Compound 3 was injected intrajugularly in the form of 2.5% solution in DMSO at a dose of 40 mg/kg (equivalent to 52.3 mg quaternary 2 or 28.2 mg testosterone). The injection was given at a rate of 44.4 μl/minute using a calibrated infusion pump. After appropriate time periods, 1 ml of blood was withdrawn from the heart and dropped immediately into a tared tube containing 5 ml acetonitrile which was later weighed to determine the weight of the blood taken. The animal was then perfused with 20 ml of saline solution, decapitated and the brain was removed. The weighed brain was homogenized with 1 ml of distilled water, 5 ml of acetonitrile was added and the mixture was rehomogenized thoroughly, centrifuged, filtered and then analyzed using the HPLC method. The tubes containing the blood were shaken vigorously, centrifuged, filtered and also analyzed using the HPLC method described at 0.05 sensitivity limit for determination of the quaternary 2 and at 0.001 sensitivity limit for determination of liberated testosterone. Quantitation was done using a recovery standard curve obtained by introducing a known amount of either compound 2 or testosterone in either brain homogenate or blood and then treated in the same manner of extraction and analysis.

EXAMPLE 9

In Vivo Brain Delivery of Testosterone Following its Administration

Female Sprague-Dawley rats with an average weight of 225±10 g were injected with testosterone at a dose level of 28.2 mg/kg following the same procedure previously described. Samples of brain and blood collected were analyzed for testosterone using HPLC.

EXAMPLE 10

In Vivo Brain Delivery of Quaternary 2 Following its Administration

Following the same procedure, female Sprague-Dawley rats were injected I.V. with the quaternary solution (0.18%) in DMSO at a dose level of 13.0 mg/kg (it was found to be toxic at higher doses). The brain samples collected were analyzed for presence of the quaternary 2 using HPLC.

EXAMPLE 11

Results of Experiments of Examples 5–10

The rates of oxidation of the dihydro derivative 3 with silver nitrate, hydrogen peroxide and diphenylpicrylhydrazyl free radical (DPP.) were determined. The reactions were carried out under pseudo first order conditions, either with higher concentrations of the oxidant in the case of hydrogen peroxide or higher concentrations of 3 in the case of the picryl reagent. With DPP., a reference sample was made using the same amounts as the test sample, but prepared 10 minutes before mixing and monitoring the test sample. This reference is used as a measure of $A_\infty$ and these were the data used to calculate the kinetic parameters. The in vitro rates of oxidation of the dihydro derivative were also determined in biological fluids, e.g. 80% plasma, whole blood, 20% brain homogenate and 20% liver homogenate. The rate of disappearance of the ester 2 and appearance of testosterone in the medium was also determined. Finally, the in vivo brain delivery and blood concentration profile of the quaternary derivative and testosterone released, against time, was determined following a single injection of the dihydropyridine derivative 3 to female rats. These results were compared to blood and brain kinetics of testosterone following administration of such.

Chemical Oxidation of the Dihydropyridine Derivative 3

(i) By Silver Nitrate: It was observed that this dihydro derivative 3 is more stable towards oxidation than the monophenethylamine type derivatives reported in my '316 application; it takes a few minutes standing for the silver to form. The product is exclusively the quaternary salt 2, as verified by the change in the UV and NMR spectra.

(ii) By Hydrogen Peroxide: At low concentrations of the dihydro compound 3 ($5 \times 10^{-6}$ M) compared to the high concentration of the peroxide (0.18 M), the oxidation proceeds according to a first order kinetics.

$$k = 2.7 \pm 0.3 \times 10^{-3} \sec^{-1} \quad t_{\frac{1}{2}} = 3.98 \pm 0.7 \text{ min} \quad r = .995$$

At higher concentrations, the dihydro compound is insoluble in $H_2O_2$.

(iii) By Diphenylpicrylhydrazl (DPP.) Free Radical: The reaction was carried out under pseudo first order conditions using excess of the dihydropyridine derivative. With the concentrations used, all runs gave good first order plots over 3 half lives, with correlation coefficient better than 0.9998.

$$k = 4.87 \pm 0.31 \times 10^{-2} \sec^{-1} \quad t_{\frac{1}{2}} = 14.1 \pm 0.6 \text{ seconds}$$

Trials to determine the second order rate constant using different concentrations of DPP. were unsuccessful.

(iv) In Vitro Oxidation and Hydrolysis in Biological Media:

Table I shows the rates, half-lives and correlation coefficient for the process of oxidation of the 1,4-dihydropyridine derivative 3 in different biological media.

The rate of hydrolysis of the quaternary 2 in 20% brain homogenate was also determined and it was found to be $3.6 \times 10^{-5} \sec^{-1}$, corresponding to a half-life, $t_{\frac{1}{2}}$, of 5:16 h.

TABLE I

Kinetics of in vitro oxidation of the dihydropyridine ester 3 to the quaternary derivative 2 in biological fluids.[a]

| Medium | k (sec$^{-1}$) | $t_{\frac{1}{2}}$ (min.) | r | Method[b] |
|---|---|---|---|---|
| 80% Plasma | $8.12 \times 10^{-5}$ | 142 | .959 | A |
| 20% Brain Homogenate | $1.72 \times 10^{-4}$ | 67 | .997 | A |
| Whole Blood | $1.74 \times 10^{-4}$ | 66 | .997 | A, B |

[a]At 37° C., initial concentration of [3] = $2.4 \times 10^{-4}$ M
[b]Method A: Following appearance of [2]
Method B: Following disappearance of [3]

(v) In Vivo Administration of Compound 3 and Testosterone:

The FIGURE of Drawing illustrates the concentration of the quaternary derivative 2 in brain and blood and concentration of testosterone released in the brain, following intravenous administration of the 1,4-dihydropyridine derivative 3. Also, the FIGURE shows the concentration of testosterone in brain and blood following administration of testosterone. The FIGURE is a graph plotting concentrations, with standard errors against time, for testosterone-17-nicotinate-N-methyl cation, calculated as iodide, in brain ( ○ ) and in blood (□) and concentration of released testosterone (ng/g) in brain (▼), all following administration of the corresponding dihydropyridine compound 3. Also plotted are concentrations of testosterone in brain (●) and blood (■) following administration of testosterone, per se.

Statistical analysis of the descending portions of the curves shown in the FIGURE provides the following results:

| (1) Rates of disappearance of the quaternary compound 2: | | |
|---|---|---|
| from brain = $2 \times 10^{-3}$ min$^{-1}$ | $t_{\frac{1}{2}}$ = 5.7 h | r = .833 |
| from blood = $1.27 \times 10^{-2}$ min$^{-1}$ | $t_{\frac{1}{2}}$ = 54 min | r = .833 |

| (2) Rate of disappearance of released testosterone following administration of dihydro compound 3 = $2.65 \times 10^{-3}$ min$^{-1}$ | | |
|---|---|---|
| $t_{\frac{1}{2}}$ = 4.4 h | r = .768 | |
| (Results analyzed for up to 5 hrs, the data shown in FIG. 4 are for 3 hrs) | | |

| (3) Rate of disappearance of testosterone following administration of testosterone: | | |
|---|---|---|
| from brain = $5.5 \times 10^{-2}$ min$^{-1}$ | $t_{\frac{1}{2}}$ = 12.6 min | r = .994 |
| from blood = $4.74 \times 10^{-2}$ min$^{-1}$ | $t_{\frac{1}{2}}$ = 14.5 min | r = .959 |

Thus, 17β-[(1,4-dihydro-1-methyl-3-pyridinylcarbonyl)oxy]androst-4-en-3-one 3 could be obtained in a high yield (more than 90%) from testosterone 17β-nicotinate by simple chemical procedures. The dihydro product obtained directly from the reduction reaction medium was found by HPLC to be quite pure and a single crystallization from hot methanol afforded an analytically pure product. No signs of oxidation were observed during crystallization, even from hot methanol, filtration or drying. The crystalline solid dihydro compound did not show signs of oxidation, decomposition or polymerization when tested by HPLC, during the 2-month shelf storage at ambient temperature under nitrogen. This compound 3 was found to be quantitatively oxidizable to the corresponding quaternary derivative 2, as identified by UV spectroscopy, whether by silver nitrate or hydrogen peroxide. The process of oxidation with silver nitrate is slower than that with the dihydropyridine derivative of phenethylamine reported in my '316 application. Oxidation with hydrogen peroxide or DPP., at pseudo first order condition, was found to take place at measurable rates ($t_{\frac{1}{2}}=3.98\pm0.7$ min and $14.1\pm0.6$ seconds, respectively) compared to the rates of oxidation of the corresponding phenethylamine and dopamine derivatives which were found to be too fast to be monitored using the same procedure. The in vitro investigation in biological fluids indicated a facile oxidative conversion of the dihydro form 3 to the corresponding quaternary 2, but at a slower rate than that of the analogous amides of phenethylamine or dopamine.

Insofar as concerns the in vivo studies of compound 3, the results shown in the FIGURE indicate that the dihydro derivative penetrates the BBB and is readily oxidized in the brain to the quaternary precursor 2. The in vivo rate of oxidation of the dihydro seems faster than that obtained from the in vitro experiment. No dihydro derivative could be detected in the brain without the sensitivity limits of the procedure. After 2 reaches its maximum concentration, within about 15 minutes, its concentration starts a decline phase corresponding to overall excretion and/or metabolism-hydrolysis. The overall rate of this phase was calculated to be $2\times10^{-3}$ min$^{-1}$ ($t_{\frac{1}{2}}=5.7$ h). In the same time, the concentration of 2 in blood was decreasing progressively from the beginning at a rate $1.27\times10^{-2}$ min$^{-1}$ or with a half life of 54 min. Equimolar administration of testosterone using the same solvent (DMSO) and the same route of administration, showed a rapid absorption of testosterone into the brain, reaching a maximum concentration within 5 minutes, followed by fast clearance from both brain and blood ($t_{\frac{1}{2}}=12.6$ min and 14.5 min respectively). The ratio of brain/blood concentration for testosterone was found to be 1.6 at 5 minutes and 1.8 at 15 minutes from administration. The ratio of brain/blood concentration of the quaternary 2 was found to increase progressively with time (3.23 at 15 min, 6.33 at 45 min and 12 at 3 hrs from administration). This indicates the predicted "lock in" property for the quaternary 2. Testosterone was found to be released from the quaternary ester 2 and could be detected in the brain following administration of the dihydro derivative 3. Analysis of the time concentration curve for release of testosterone indicated two phase kinetics for disappearance from the brain. The first phase is a fast descending one at a rate of $1.2\times10^{-2}$ min$^{-1}$ followed by a slow clearance phase with a rate of $5.8\times10^{-4}$ min$^{-1}$ and a half life of about 20 hrs which corresponds to about 130 hrs for complete clearance from the brain. This result, if compared to that obtained by H. Frey, A. Aadvaag, D. Saahum and J. Falch, *Eur. J. Clin. Pharmacol.*, 16, 345 (1979), for the clearance of testosterone from plasma after oral administration (about 6 hrs), is very promising. Although the concentrations of testosterone in the brain following administration of compound 3 are low compared to that following administration of testosterone, this is by no means a disadvantage because such high concentration of testosterone may not be needed for receptor saturation. By dose manipulation of the dihydro derivative, a concentration of testosterone just sufficient for receptor saturation for a delayed period could be attained.

Similarly designed in vivo studies of compound 3 in male rats should show analogous "locking in" of the quaternary 2 in the testes following administration of the dihydro compound, as well as release of testosterone from the quaternary and detection of testosterone in the testes following administration of the dihydro derivative.

Accordingly, provided hereby are not only a generic method and novel class of pro-prodrugs for the specific and/or target enhanced delivery to the testes of a variety of drug species via the bidirectional transport of the drug species into and out of the testes employing dihydropyridine⇌pyridinium salt carrier redox systems, but also a system providing insight into the basic transport processes (both active and passive) of, and enzymatic activities in, the blood-testis barrier, as well as into the various processes specific to the function of the testes. Again, another very significant aspect of the bioreversible redox delivery system according to this invention is the toxicity implication, for significantly reduced is systemic toxicity by accelerating the elimination of the drug/quaternary carrier system. And even central toxicity is reduced by providing for low level, sustained release of the active drug species in the testes. Low toxicity is provided both as regards the quaternary carrier and in combination with the drug.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A method for site-specifically and sustainedly delivery a testicularly acting drug species to the testes, comprising administering to a male mammal in need of such treatment a quantity of a compound having the formula

[D—DHC]  (I)

or a non-toxic pharmaceutically acceptable salt thereof, wherein [D] is testicularly acting drug species and [DHC] is the reduced, biooxidizable, lipoidal form of a dihydropyridine⇌pyridinium salt redox carrier, said redox carrier facilitating the transport of said testicularly acting drug species across the blood-testis barrier and delivering said testicularly acting drug species to the testes in a site-specific and sustained manner, said quantity being sufficient to deliver a testicularly, pharmacologically effective amount of said testicularly acting drug species to the testes.

2. A method as defined by claim 1 for site-specifically and sustainedly delivering an androgenic drug species to the testes, comprising administering to a male mammal in need of such treatment a quantity of a compound having the formula

[D—DHC]   (I)

or a non-toxic pharmaceutically acceptable salt thereof, wherein [D] is an androgenic drug species and [DHC] is the reduced, biooxidizable, lipoidal form of a dihydropyridine⇌pyridinium salt redox carrier, said redox carrier facilitating the transport of said androgenic drug species across the blood-testis barrier and delivering said androgenic drug species to the testes in a site-specific and sustained manner, said quantity being sufficient to deliver an androgenically effective amount of said androgenic drug species to the testes.

3. A method as defined by claim 1, wherein [D] is a testicularly acting drug species and [DHC] is the reduced, biooxidizable, blood-testis barrier penetrating, lipoidal form of a dihydropyridine⇌pyridinium salt redox carrier, with the proviso that when [DHC] is

[structure: 1-methyl-3-acetyl-1,4-dihydropyridine]

then [D] cannot be testosterone.

4. A method as defined by claim 1, wherein [D] is a testicularly acting antibacterial.

5. A method as defined by claim 1, wherein [D] is a testicularly acting antiviral agent.

6. A method as defined by claim 1, wherein [D] is a testicularly acting analgesic.

7. A method as defined by claim 1, wherein [D] is a testicularly acting antitumor or anticancer agent.

8. A method as defined by claim 1, wherein [D] is a testicularly acting hormonal agent.

9. A method as defined by claim 7, wherein [D] is a nitrogen mustard.

10. A method as defined by claim 9, wherein [D] is chlorambucil.

11. A method as defined by claim 9, wherein [D] is melphalan.

12. A method as defined by claim 7, wherein [D] is a folic acid antagonist.

13. A method as defined by claim 12, wherein [D] is methotrexate.

14. A method as defined by claim 7, wherein [D] is a platinum coordination complex.

15. A method as defined by claim 14, wherein [D] is a cisplatin analogue.

16. A method as defined by claim 7, wherein [D] is an antibiotic anticancer agent.

17. A method as defined by claim 16, wherein [D] is dactinomycin.

18. A method as defined by claim 7, wherein [D] is a hormonal anticancer agent.

19. A method as defined by claim 8, wherein [D] is a pituitary or nonpituitary gonadotropin.

20. A method as defined by claim 8, wherein [D] is a glucocorticoid steroid.

21. A method as defined by claim 8, wherein [D] is testosterone.

22. A method as defined by claim 8, wherein [D] is methyltestosterone.

23. A method as defined by claim 8, wherein [D] is an antiandrogen.

24. A method as defined by claim 3, wherein [DHC] comprises the reduced form of a nicotinic acid derivative.

25. A method as defined by claim 3, wherein [DHC] comprises the reduced form of a trigonelline.

26. A method as defined by claim 3, wherein [DHC] comprises the reduced form of an isoquinoline.

27. The method as defined by claim 3, wherein [DHC] comprises the reduced form of a pyridinium alcohol.

28. A method as defined by claim 3, wherein [DHC] is (i), (ii), (iii), (iv), (v), (vi), (vii) or (viii)

wherein the $$-\overset{O}{\underset{\|}{C}}-, \quad -CH_2\overset{O}{\underset{\|}{C}}- \quad \text{and} \quad -CH_2-\overset{O}{\underset{\|}{O}C}-$$

substituents in formulae (i), (ii) and (iii) each can be in the 2-, 3- or 4- position on the ring, $R_1$ is $C_1$-$C_7$ alkyl or $C_7$-$C_{10}$ aralkyl and $R_3$ is $(CH_2)_n$ wherein n is 1, 2 or 3.

29. A method as defined by claim 28, wherein [DHC] is

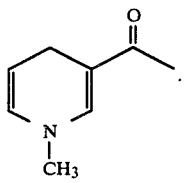

30. A method as defined in claim 3, wherein [D] is chlorambucil, melphalan, methotrexate, a cisplatin analogue, dactinomycin, testosterone or a testosterone analogue.

31. A method as defined by claim 2 wherein [DHC] is

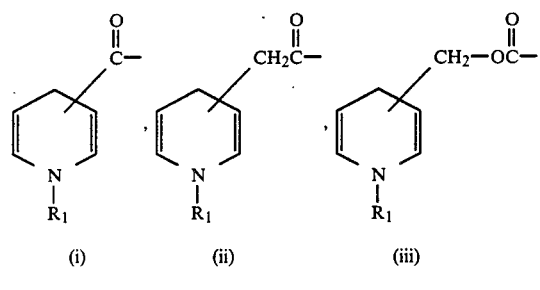

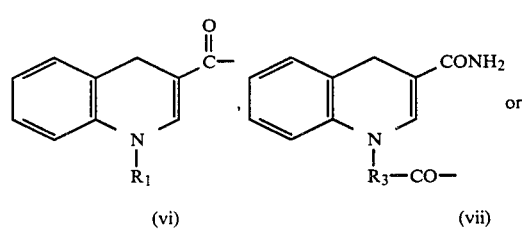

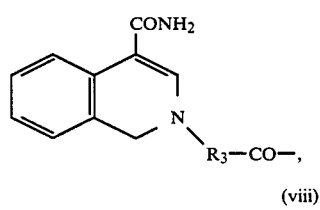

wherein the

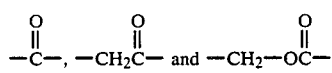

32. A method as defined in claim 2 wherein [DHC] is

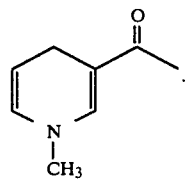

33. A method as defined by claim 2 wherein [D] is the residue of testosterone or of methyl testosterone, said residue having the formula

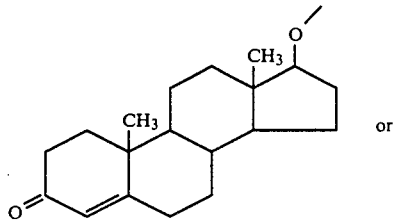

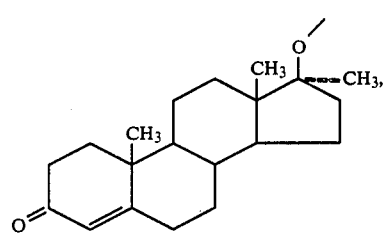

respectively.

34. A method as defined by claim 31 wherein [D] is the residue of testosterone or of methyl testosterone, siad residue having the formula

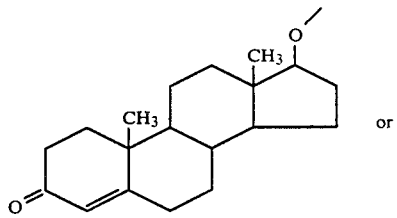

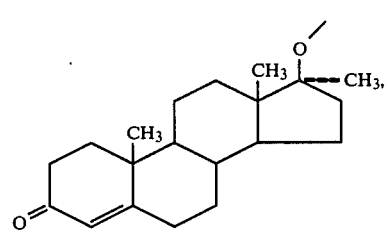

respectively.

35. A method as defined by claim 32 wherein [D] is the residue of testosterone or of methyl testosterone, said residue having the formula.

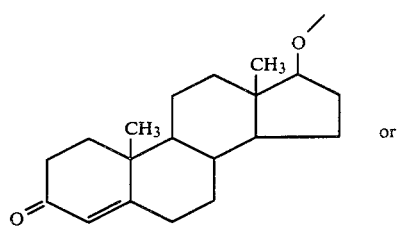

or

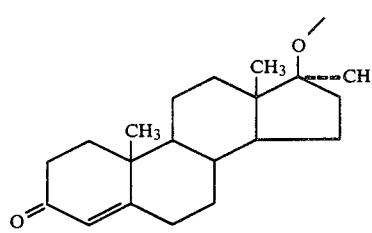

respectively.

36. A method as defined by claim 35 for site-specifically and sustainedly delivering testosterone to the testes, comprising administering to a male mammal in need of such treatment a quantity of a compound of the formula

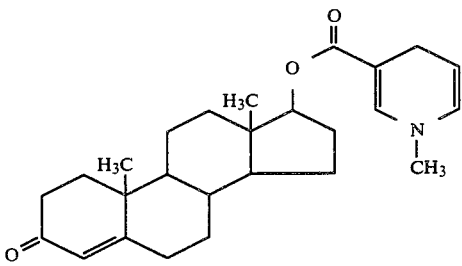

or a non-toxic pharmaceutically acceptable salt thereof, said quantity being sufficient to deliver an androgenically effective amount of testosterone to the testes.

37. A method as defined by claim 36 wherein the compound administered is 17β-[(1,4-dihydro-1-methyl-3-pyridinylcarhonyl)oxy]androst-4-en-3-one.

* * * * *